(12) United States Patent
Löffler et al.

(10) Patent No.: US 10,765,444 B2
(45) Date of Patent: Sep. 8, 2020

(54) MEDICAL INSTRUMENT FOR ABLATION OF TISSUE

(71) Applicant: Karl Storz SE & Co. KG, Tuttlingen (DE)

(72) Inventors: Oliver Löffler, Boll (DE); Stefan Rehbein, Immendiegen-Hattingen (DE); Uwe Wittke, Tuttlingen-Möhringen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 161 days.

(21) Appl. No.: 16/031,634

(22) Filed: Jul. 10, 2018

(65) Prior Publication Data

US 2019/0015128 A1    Jan. 17, 2019

(30) Foreign Application Priority Data

Jul. 13, 2017 (DE) .................. 10 2017 115 778

(51) Int. Cl.
*A61B 18/14* (2006.01)
*A61B 17/32* (2006.01)
(Continued)

(52) U.S. Cl.
CPC ...... *A61B 17/320016* (2013.01); *A61B 18/14* (2013.01); *A61B 18/149* (2013.01);
(Continued)

(58) Field of Classification Search
CPC ............ A61B 17/320016; A61B 18/14; A61B 18/1485; A61B 18/149; A61B 18/201;
(Continued)

(56) References Cited

U.S. PATENT DOCUMENTS 6,024,751 A    2/2000  Lovato et al.
6,245,011 B1   6/2001  Dudda et al.
(Continued)

FOREIGN PATENT DOCUMENTS

DE    4301249 A1     10/1993
DE    693 33 489 T2   4/2005
(Continued)

OTHER PUBLICATIONS

Search Report, DE 10 2017 115 778.6, dated Jan. 29, 2018 (9 pp.).
Search Report, DE 18175958.01, dated Dec. 19, 2018 (7 pp.).

*Primary Examiner* — George Manuel
(74) *Attorney, Agent, or Firm* — Eversheds Sutherland (US) LLP

(57) ABSTRACT

The present application discloses a medical instrument for tissue ablation by a minimally invasive surgical procedure, including a hollow outer shaft, an inner shaft which can be guided longitudinally displaceably in the hollow outer shaft, and a control portion at a proximal end of the medical instrument, in order to position the hollow outer shaft. An attachment for mechanical ablation of tissue is arranged at a distal end of the inner shaft, wherein the attachment does not protrude beyond an inner profile formed by the inner faces of the outer shaft, and wherein at any rate the distal end of the attachment protrudes beyond the distal end of the hollow outer shaft in order to ablate tissue. The medical instrument may be combined with further medical appliances, in particular with an HF coagulation attachment or a laser coagulation attachment for tissue coagulation.

20 Claims, 8 Drawing Sheets

(51) Int. Cl.
*A61B 18/20* (2006.01)
*A61B 18/00* (2006.01)
*A61B 17/00* (2006.01)
*A61B 18/22* (2006.01)
*A61B 90/00* (2016.01)

(52) U.S. Cl.
CPC ........ *A61B 18/1485* (2013.01); *A61B 18/201* (2013.01); *A61B 18/22* (2013.01); *A61B 2017/00274* (2013.01); *A61B 2017/320004* (2013.01); *A61B 2017/320064* (2013.01); *A61B 2018/00196* (2013.01); *A61B 2018/00547* (2013.01); *A61B 2018/00577* (2013.01); *A61B 2018/00589* (2013.01); *A61B 2018/00982* (2013.01); *A61B 2018/1407* (2013.01); *A61B 2018/1475* (2013.01); *A61B 2090/0817* (2016.02); *A61B 2217/007* (2013.01)

(58) Field of Classification Search
CPC .......... A61B 18/22; A61B 2017/00274; A61B 2017/320004; A61B 2017/320064; A61B 2018/00196; A61B 2018/00547; A61B 2018/00577; A61B 2018/00589; A61B 2018/00982; A61B 2018/1407; A61B 2018/1475; A61B 2090/0817; A61B 2217/007
See application file for complete search history.

(56) References Cited

U.S. PATENT DOCUMENTS

| | | |
|---|---|---|
| 2012/0150179 A1 | 6/2012 | Feinberg et al. |
| 2014/0180122 A1* | 6/2014 | Stigall .................. A61B 5/6852 600/467 |
| 2015/0164424 A1* | 6/2015 | Byrd .................... A61B 5/0071 600/317 |

FOREIGN PATENT DOCUMENTS

| | | |
|---|---|---|
| DE | 10 2006 039 696 A1 | 2/2008 |
| DE | 2016018457 A1 | 1/2018 |
| EP | 2 298 204 B1 | 3/2011 |
| WO | 2016018457 A1 | 2/2016 |

\* cited by examiner

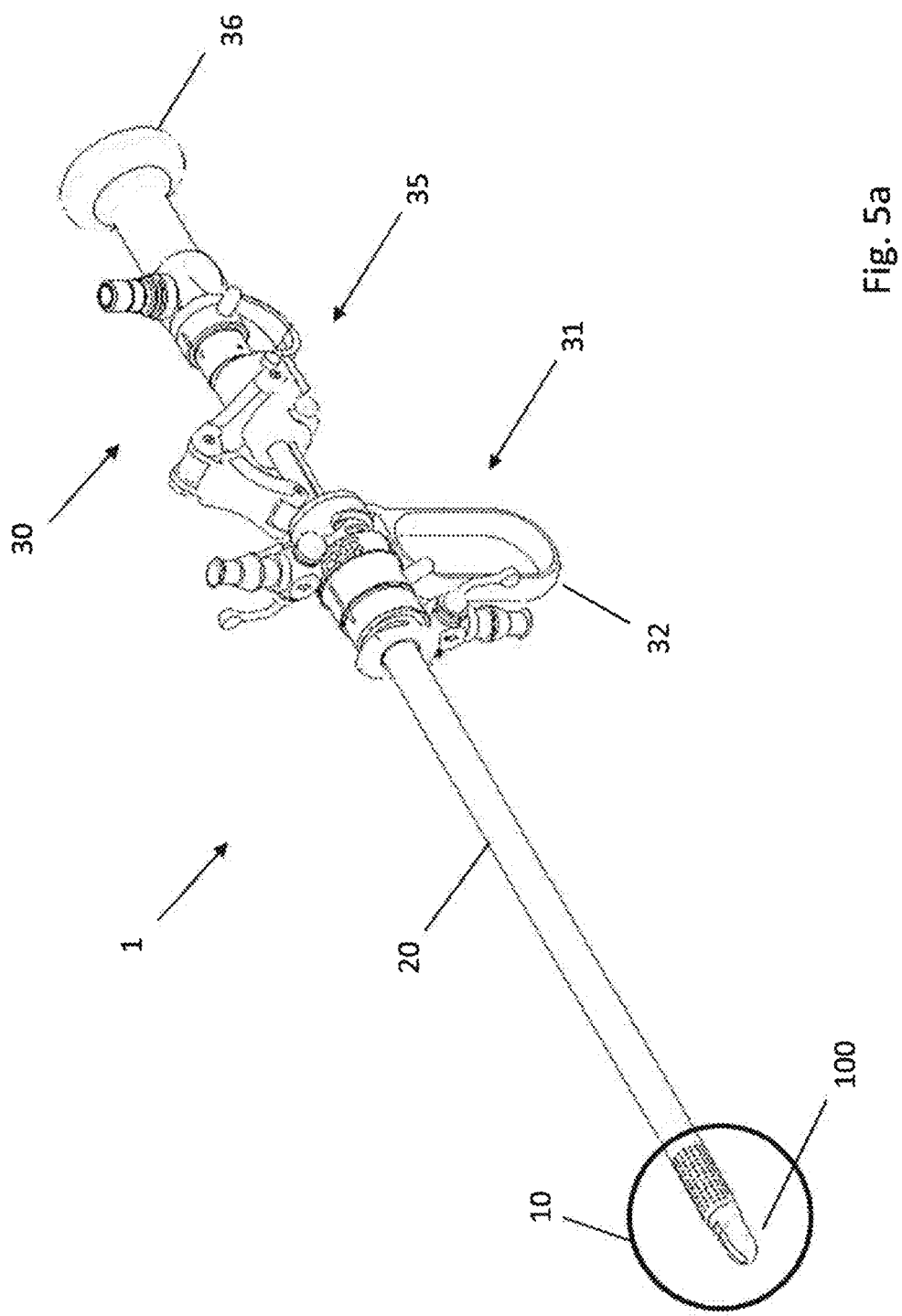

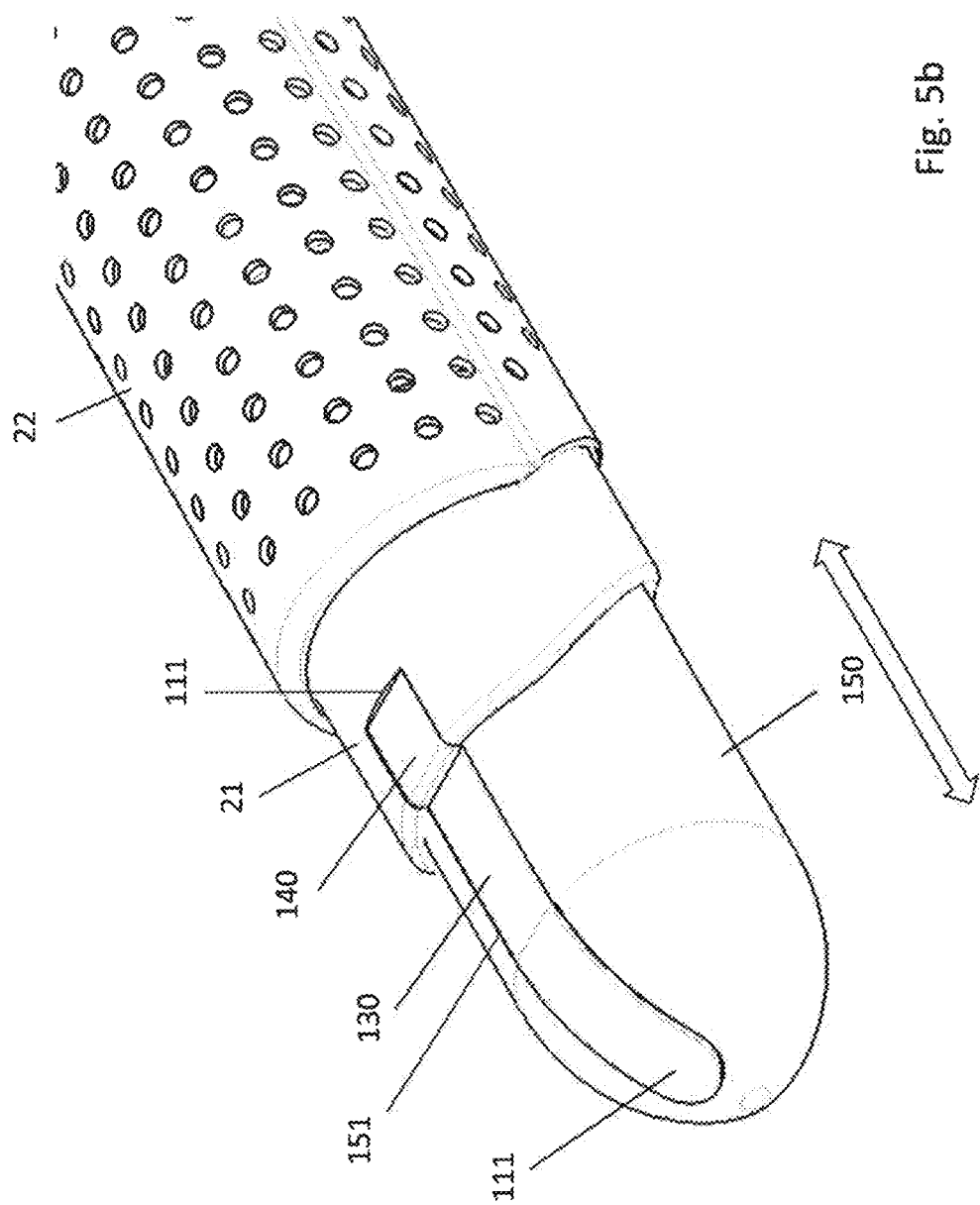

MEDICAL INSTRUMENT FOR ABLATION OF TISSUE

The invention relates generally to a medical instrument for minimally invasive surgery, in particular to a medical instrument for resectoscopy, cold enucleation of tissue, in particular of prostate tissue, by a minimally invasive surgical procedure.

BACKGROUND OF THE INVENTION

It is nowadays no longer possible to imagine modern medicine without minimally invasive procedures. In the field of resectoscopy, in which harmful or damaged tissue is removed (e.g. from the prostate), particular use is made of resectoscopes that have a high-frequency cutting means with which tissue is ablated by high-frequency currents. An advantage of tissue ablation by means of high-frequency currents is that bleeding at the operating site can be rapidly staunched.

DE 2006 039 696 A1 discloses a device for resection and/or ablation of organic tissue by means of high-frequency current. The device comprises a coil, which can be subjected to a high-frequency voltage, and a coil carrier, which is configured as a cylindrical hollow tube. The coil is arranged at a distal end of the coil carrier, wherein a coil end portion of the coil and a distal connecting element portion form a wedge-shaped cutting edge to which the high-frequency voltage can be applied. Since the coil is made of an electrically conductive wire, it can deform at the operation site even under the action of a slight force, which makes precise ablation of tissue difficult.

DE 693 33 489 T2 discloses a medical probe device which comprises a catheter and a flexible stylet, wherein the stylet is guided in a corresponding guide housing. For tissue ablation, a high-frequency electrode (also referred to sometimes as a needle) can be arranged on the stylet. Although said device brings with it a great many additional possibilities, mechanical ablation of tissue is again not possible here, since the high-frequency electrode deforms at the application site even under the action of a slight force.

EP 2 298 204 B1 from the applicant discloses a medical instrument for bipolar electrosurgery, with an outer shaft, at the distal end of which an electrically conductive blade is arranged which is insulated from the outer shaft, and with a working insert which is received in the outer shaft and can be moved axially to and fro in the latter and, at its distal end, has a hook with a cutting edge directed outward in the proximal direction. In a deployed position of the working insert, tissue can be gripped by the hook and can be moved in the direction of the blade by pulling the working insert into the outer shaft. When a high-frequency current is applied to the hook and blade, tissue held between them is coagulated. By pulling the working insert farther into the outer shaft, it is also possible to separate tissue. Since the cutting edges of hook and blade are at an angle to each other, a scissor-like cutting movement can be executed between the cutting edges of hook and blade. However, the construction and the operating behavior of this medical instrument are relatively complicated.

Moreover, the prior art also discloses cutting instruments for minimally invasive surgery which are secured on an outer shaft of an endoscope, resectoscope or a needle.

U.S. Pat. No. 6,245,011 B1 discloses such an endoscopic cutting instrument comprising a radially adjustable blade which is arranged at a distal end of the outer shaft of the instrument and can be deployed radially beyond the outer shaft such that, by means of a rotational movement, it can be used to cut in a circumferential direction.

In summary, the instruments from the prior art have in particular the disadvantage that no mechanical ablation of tissue is possible in an axial direction.

DESCRIPTION OF THE INVENTION

It is therefore an object of the present invention to make available a medical instrument for mechanical ablation or abrasion of tissue by a minimally invasive surgical procedure, with which tissue can be abraded or ablated in a targeted manner in an axial direction, said instrument being able to be safely guided to the operating site.

The object is achieved by the medical instrument according to the invention as per Claim 1. Further advantageous embodiments are set forth in the subclaims.

According to a preferred embodiment, the present invention discloses a medical instrument for mechanical ablation or abrasion of tissue by a minimally invasive surgical procedure, which medical instrument has a hollow outer shaft and an inner shaft, wherein a control portion is arranged at a proximal end of the medical instrument and is configured for positioning the hollow outer shaft suitably at the operating site. According to the invention, an attachment for mechanical ablation of tissue is arranged directly at a distal end of the inner shaft, wherein the attachment does not protrude radially beyond an inner profile formed by the inner faces or the inner circumferential wall of the outer shaft, and wherein the distal end of the attachment protrudes axially beyond the distal end of the hollow outer shaft in order to ablate tissue.

For this purpose, the inner shaft may in principle be immovable relative to the hollow outer shaft, in order to be positioned together with the latter for positioning the attachment for tissue ablation at the operating site. However, according to a preferred embodiment, the inner shaft is axially adjustable relative to the hollow outer shaft.

The words "proximal" and "distal" are used below in the manner customary in medical terminology. In relation to the medical instrument, "proximal" also means toward the operator, i.e. away from the operating site, and "distal" means toward the operating site, i.e. away from the operator. In other words, forward and rearward in the longitudinal direction of the medical instrument as seen from the control portion.

As described above, the outer shaft is hollow, i.e. tubular, in particular cylindrical, if appropriate oval or elliptic, in order to guide the inner shaft therein. The outer shaft is used for the insertion into and positioning in the human body. For this purpose, the proximal control portion can preferably comprise a handle, which in particular can also be a positioning handle and is coupled to the outer shaft such that a distal end of the medical instrument can be guided precisely to the operating site in the human body. The outer shaft is conceived here as a component part of a microinvasive instrument, examples of such instruments being microinvasive instruments, endoscopes, needles, and preferably also resectoscopes. An endoscope can be inserted together with this instrument or in a clear cross section of this instrument.

According to a further embodiment, the inner shaft of the medical instrument is guided longitudinally displaceably in the outer shaft but can be locked axially in one or more positions, if appropriate also steplessly. Tight guiding is conceivable here, in which the outer wall of the inner shaft bears tightly on the inner wall of the outer shaft and in particular slides thereon. Alternatively, other types of guiding are also conceivable in which the inner shaft is not guided by bearing tightly in the outer shaft, and instead additional guide means are provided for the precision guiding of the inner shaft in the longitudinal direction in the hollow outer shaft. The inner shaft can in this case have both a round cross section, for example a circular cross section, and also an elliptical cross section.

An important component part of the medical instrument is the attachment, secured at the distal end, for mechanical ablation, abrasion, removal or detachment of tissue, hereinafter ablation, wherein the attachment is preferably configured in the form of a lug protruding in the axial and radial directions. This attachment permits mechanical ablation of tissue through movement of the attachment relative to the tissue that is to be ablated at the operating site. For this purpose, the inner shaft, hence also the attachment, is preferably moved forward and backward. By virtue of the solid, mechanically stable construction of the attachment, a relatively high force can be applied to the distal end of the attachment. In this way, solid tissue parts can also be ablated (relatively) quickly. The attachment is thus suitable for wide-reaching ablation of undesired tissue, dead tissue or damaged tissue (with poor blood circulation).

For tissue ablation by means of the attachment, an adjustment of the outer shaft together with the inner shaft can in principle take place. In a special case, however, the movement of the attachment is effected by adjustment of the inner shaft relative to the hollow outer shaft, by actuation of the control portion. An incision opening of the outer shaft in this case serves as a virtually stationary reference region which is suitably positioned with respect to the operating site, in particular also at a suitable angle of the attachment relative to the tissue that is to be ablated, and the actual tissue ablation takes place through adjustment of the inner shaft relative to the hollow outer shaft by means of the control portion, which for this purpose can also have a suitable step-up or step-down transmission in order for a movement of a sub-portion of the control portion relative to a further sub-portion of the control portion, which is adjustable relative to the latter to be stepped up or stepped down, which as a whole permits a very precise adjustment of the attachment.

If the inner shaft has a circular cross section, a rotation movement of the inner shaft relative to the outer shaft is also possible. This rotation movement can be used, for example, for lateral abrasion, ablation or cutting of tissue or can merely serve for further positioning of the attachment.

In a preferred embodiment, the control portion is connected to the inner shaft such that the attachment can be retracted fully into the hollow outer shaft and, to permit tissue ablation, the attachment at least partially protrudes axially beyond a distal end of the hollow outer shaft.

Through this retraction of the inner shaft, hence also of the attachment for tissue ablation, it is possible to ensure that the attachment for tissue ablation can be guided safely to the operating site, without damaging healthy tissue on the way there. Once it has arrived at the operating site, the attachment for tissue ablation can then be axially deployed in order to commence the ablation. In order to ablate tissue, the distal end of the attachment has to be driven at least partially out of the outer shaft in order to come into contact with the tissue that is to be ablated. Preferably, however, the entire attachment protrudes from the hollow outer shaft in its position of maximum deployment.

In a preferred embodiment, the attachment of the medical instrument comprises a rectilinearly extending portion, which is connected to the distal end of the inner shaft. In this way, with a predefined axial adjustment of the inner shaft relative to the outer shaft, the attachment can protrude maximally from the hollow outer shaft in order to ablate tissue. A distal end of the attachment preferably extends at an inclination to the rectilinear portion. In other words, the distal end of the attachment is thus inclined toward a center line of the medical instrument. This configuration has the effect that, upon adjustment of the inner shaft, the attachment does not simply penetrate the tissue in front of the distal end of the hollow outer shaft. Rather, the inclined distal portion can be moved over a tissue portion in a controlled sliding motion in order to ablate tissue, in particular to enucleate tissue, and the location of the attachment can be monitored at any time by a suitable imaging lens system.

According to a preferred further embodiment, the inclined distal end of the attachment does not extend beyond the aforementioned instrument center line, or the center line of the hollow outer shaft, and therefore only a maximum of one half of the tissue region in the continuation of the hollow outer shaft can be reached by the attachment. The other half of this tissue region can of course be reached through simple rotation of the hollow outer shaft. Overall, more precise tissue ablation can thus be achieved.

In a preferred embodiment, the attachment thus extends toward the instrument center line by at most 50% and particularly preferably by 40% of the internal diameter of the hollow outer shaft.

According to a further embodiment, the rectilinear portion of the attachment is adjoined by an arcuately curved or angled portion at whose distal end an ablation edge is provided, which preferably extends at right angles to the underside or top of the distal end of the arcuately curved or angled portion. The lug-shaped configuration of the attachment is similar to a (sledge) runner and is curved or angled toward the front. More precisely, the distal end is curved at an angle toward the center line of the outer shaft, wherein the curved or angled portion encloses an angle with the rectilinear portion. This angle can be between 115° and 155°, preferably between 120° and 150°, more preferably between 130° and 140°. The aforementioned ablation edge thus likewise extends at an inclination to the center line of the hollow outer shaft, preferably at an angle of approximately 45° to the center line of the hollow outer shaft, which makes the ablation of tissue more efficient and in particular permits effective enucleation. For this purpose, the ablation edge is as far as possible right-angled, with the smallest possible radius of curvature of the ablation edge.

By virtue of this advantageous design, the operator is able to slide the rectilinear proximal part of the attachment over tissue and to ablate any projecting tissue with the angled ablation edge of the device, if this tissue projects. That is to say, an incision into healthy tissue, which lies in a deeper tissue layer, is made difficult, as a result of which undesired damage can be efficiently avoided. Consequently, the device permits targeted ablation, in particular of tissue projecting in relation to the center line of the outer shaft, in particular of tissue that at least partially extends perpendicularly with respect to this center line. The choice of angle can be suitably made according to the tissue layer that is to be ablated.

According to a further embodiment, the ablation edge of the medical instrument extends substantially perpendicularly with respect to an underside of the distal end. This embodiment is particularly advantageous for the ablation of easily separable tissue, since upper tissue layers can be safely abraded. According to further embodiments, however, blade-like ablation edges are also possible, which are used in particular if more solid tissue is to be separated, e.g. cancerous tissue in the prostate.

According to a preferred embodiment, the axial length of the attachment, calculated from the distal end of the inner shaft, lies in the range of between 1 mm and 16 mm, preferably in the range of between 3 mm and 13 mm, more preferably in the range of between 5 mm and 11 mm, although other lengths are also conceivable. Two factors are to be considered when choosing the axial length. A longer attachment makes it possible to abrade a larger region and, with the outer shaft positioned, to penetrate farther into the tissue. However, too long an outer shaft also results in increasing instability and decreased operating precision of the attachment. This is because the operator normally uses an imaging lens system for orientation, which lens system (in this case) is arranged in the inner shaft; if the ablation edge moves too far away from the camera, the ablation region can then no longer be adequately observed or may lie outside the focus range of the imaging lens system. The aforementioned range is a resulting optimized range.

According to a further embodiment, the attachment is welded onto the distal end of the inner shaft, in particular in the region of a cutout which is formed at the distal end of the inner shaft. This permits excellent stability of the attachment on the medical instrument, in order to reliably exclude loss or lateral deflection of the attachment during an operation. However, other non-releasable or even releasable fastening means are possible in principle, in particular a releasable latch mechanism, for example in order to permit simple replacement of the attachment by another attachment with another shape.

According to a further embodiment, the inner shaft is guided longitudinally displaceably in the hollow outer shaft, and the control portion is moreover configured for adjusting the position of the inner shaft relative to the hollow outer shaft. The control portion can in particular be coupled to the inner shaft such that the attachment can be retracted fully into the hollow outer shaft, for example for the insertion of the attachment into human tissue, and such that the attachment at least partially protrudes axially beyond the distal end of the hollow outer shaft in order to permit tissue ablation. In this way, damage to tissue during the insertion of the attachment into human tissue can be effectively avoided.

According to a further embodiment, the inner shaft can for this purpose be guided longitudinally displaceably and rectilinearly in the outer shaft, as a result of which an uncontrolled rotation of the inner shaft relative to the outer shaft is efficiently prevented and the attachment can be guided more precisely to the operating site and can be suitably positioned there. In an advantageously simple manner, such rectilinear guiding can be achieved by the fact that the outer profile of the inner shaft is not rotationally symmetrical, in particular in the form of an oval or elliptical outer profile, wherein the inner profile of the outer shaft is configured corresponding to the outer profile of the inner shaft.

According to a further embodiment, the inner shaft of the medical instrument is configured as a hollow tube. In this embodiment, it is possible to guide further instruments to the operating site, for example HF electrodes, cameras, imaging optics or further cutting instruments. Combination instruments are thus made possible.

According to a further embodiment, an elongate receiving element with a cutout or seat is moreover provided for temporarily receiving the attachment for mechanical ablation of tissue, wherein the elongate receiving element is axially adjustable relative to the hollow inner shaft between a deployed position, in which the attachment for mechanical ablation of tissue is temporarily received in the cutout or seat, and a retracted position, in which the attachment for mechanical ablation of tissue protrudes axially beyond the distal end of the hollow outer shaft and is accessible for tissue ablation.

According to a further preferred embodiment, an HF coagulation attachment for coagulating tissue by application of a high-frequency (HF) voltage is moreover provided at the distal end of the inner shaft. This HF coagulation attachment can be connected fixedly to the instrument, although in principle it can also be axially adjustable relative to the hollow inner shaft, or it can be inserted into the hollow inner shaft subsequently, for example after insertion of the instrument attachment into the human tissue and after positioning thereof at the operating site. The medical instrument is thus extended to give a combination instrument that permits various operating modes. This can be particularly useful if the mechanical ablation of tissue gives rise to bleeding. By means of the coagulation with the HF coagulation attachment, said bleeding can then be easily stopped, without the inner shaft first having to be guided with the attachment out of the hollow outer shaft and replaced by a coagulation attachment.

According to a further embodiment, the HF coagulation attachment for this purpose has a coil to which a high-frequency voltage can be applied for tissue coagulation, which coil protrudes axially from the distal end of the inner shaft to a lesser extent than the attachment for mechanical ablation of tissue and is electrically insulated from the inner shaft. Mechanical protection of the coil is thus realized in a simple manner by the attachment, for example during the insertion of the instrument attachment into human tissue. The coil can have a connecting portion and an arcuately curved loop at the distal end of the connecting portion, wherein the arcuately curved loop extends substantially parallel to the distal end of the inner shaft, in particular at an inclination to the instrument center line, as a result of which an axial adjustment length for driving the HF coagulation attachment beyond the distal end of the hollow inner shaft can be easily minimized.

According to a further embodiment, seen in a side view of the distal end of the medical instrument, the arc-shaped loop and the distal end of the inner shaft extend at an inclination and toward the proximal end of the hollow inner shaft, as a result of which a wedge-shaped, inclined working end of the HF coagulation attachment can be easily realized for coagulating tissue in front of the distal end of the inner shaft.

According to a further embodiment, a laser coagulation attachment for coagulating tissue by laser radiation is provided as an alternative to the aforementioned HF coagulation attachment at the distal end of the inner shaft. The laser coagulation attachment can protrude axially from the distal end of the inner shaft, and, according to this embodiment too, a distal end of the laser coagulation attachment protrudes from the distal end of the inner shaft less far than the attachment for mechanical ablation of tissue. This laser coagulation attachment can be connected fixedly to the instrument, although in principle it can also be axially adjustable relative to the hollow inner shaft, or it can be inserted into the hollow inner shaft subsequently, for example after insertion of the instrument attachment into the human tissue and after positioning thereof at the operating site.

BRIEF DESCRIPTION OF THE DRAWINGS

Preferred embodiments are described below with reference to the attached drawings, in which:

FIG. 3b shows a greatly enlarged perspective view of the distal region of the medical instrument according to FIG. 3a;

FIG. 3c shows a greatly enlarged side view of the distal region of the medical instrument according to FIG. 3a;

FIG. 4b shows a greatly enlarged perspective view of the distal region of the medical instrument according to FIG. 4a;

FIG. 4c shows a greatly enlarged side view of the distal region of the medical instrument according to FIG. 4a;

FIG. 5a shows a perspective view of a medical instrument according to a further embodiment of the present invention;

FIG. 5b shows the detail according to FIG. 5a in a greatly enlarged perspective view;

In the figures, identical reference signs designate identical or substantially equivalent elements or element groups.

DETAILED DESCRIPTION OF THE DRAWINGS

Figure 1:
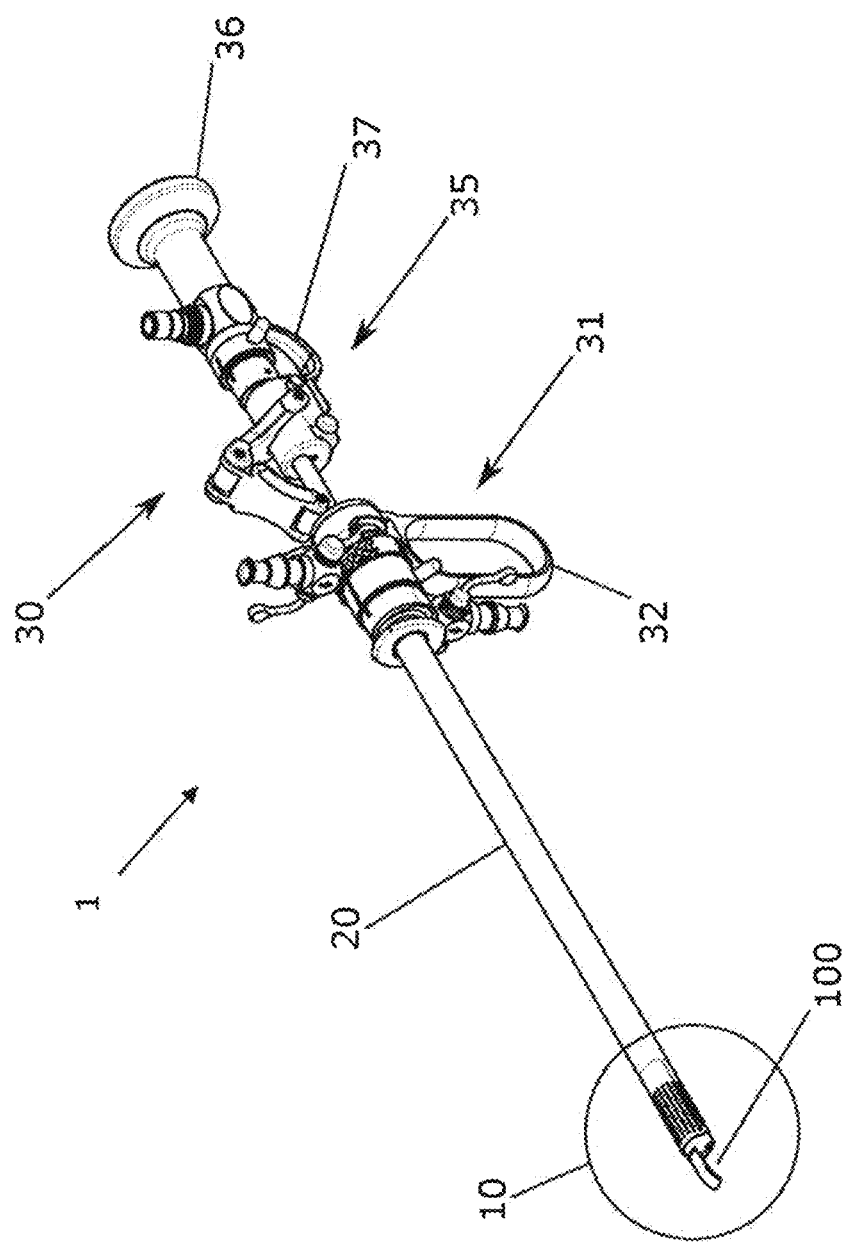
FIG. 1 shows a schematic view of a medical instrument according to a preferred embodiment of the present invention.

FIG. 1 shows a medical instrument 1 for ablation of tissue, in particular prostate tissue, by a minimally invasive surgical procedure according to a preferred embodiment of the present invention. The medical instrument 1 has substantially three portions: a front or distal portion 10, a control portion 30 located at a rear or proximal end, and a portion which is formed by the shaft 20, extends between the aforementioned portions and is connected to each of these.

The distal end 10 is located at the front end of the shaft 20 and comprises in particular a front opening of the shaft 20. A lug-shaped attachment 100 is arranged on an outer wall of the shaft 20 and serves for tissue ablation.

The shaft 20 has a substantially cylindrical shape and is of a suitable length and size to be inserted into a human body. In an alternative configuration, the shaft can also have an oval shape or other tube shape, as is described below with reference to FIGS. 6a to 7b. In a minimally invasive surgical procedure, the shaft 20 can be used to insert operating instruments into the human body to the site of an operation.

The control portion 30 has substantially two sub-portions, namely a positioning handle portion 31 and an operating handle portion 35, which are connected to each other in a longitudinally movable manner via a transmission rod, for transmission of a force, and a positioning hinge, for the positioning and guiding of the shaft.

At the positioning handle portion 31 located at the distal end of the control portion 30, a positioning handle 32 is in particular arranged which can be rigidly connected to the outer part of the shaft 20. In this way, the positioning handle 32 can be used to insert the medical instrument 1 into the human body and to position it at the operating site.

An eyepiece 36 and an operating handle 37 are arranged on the operating handle portion 35 at the proximal end of the control portion. The operator (i.e. the surgeon) is now able to guide his thumb through the operating handle 37 and the other fingers of one hand through the positioning handle 32 and, by opening and closing his hand, to execute a forward and rearward movement of an inner shaft relative to the hollow outer shaft of the shaft 20, such that the operator is able to operate with just one hand.

With the aid of the operating handle 37, parts of the medical instrument 1 can additionally be rotated.

Consequently, the medical instrument 1 according to this embodiment is thus a resectoscope with an additional attachment 100 for mechanical ablation of tissue. However, the attachment 100 can also be arranged on other similar medical instruments, particularly if they have the movable inner shaft 21 described below.

Figure 2A:
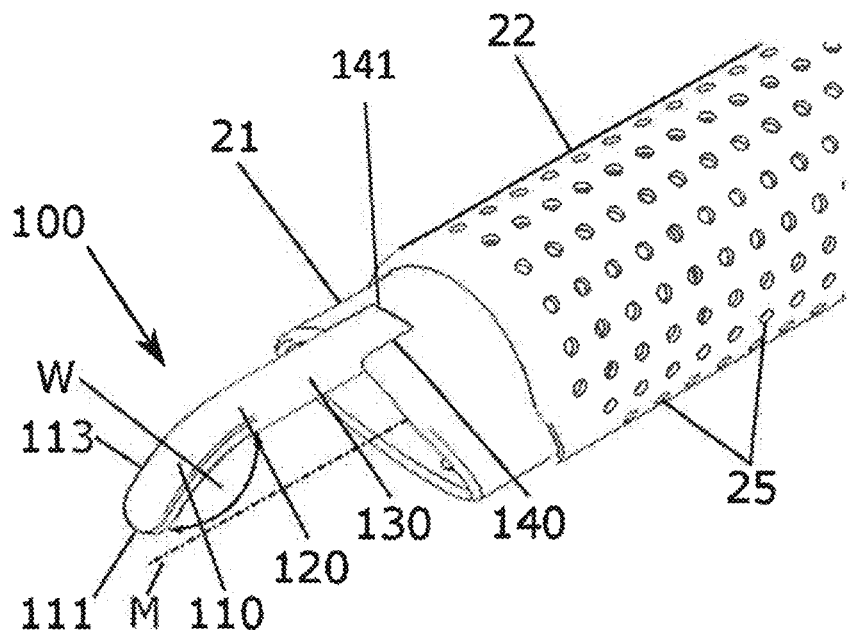
FIG. 2a shows a schematic view of the distal region of the medical instrument with a forwardly curved ablation edge according to a preferred embodiment of the present invention.

FIG. 2a shows a detailed view of the distal end 10 of a preferred embodiment of the present invention. An attachment 100 for tissue ablation is arranged at the distal end of an inner shaft 21, which is guided longitudinally displaceably in a hollow outer shaft 22. The aforementioned shaft 20 thus comprises an outer shaft 22 and an inner shaft 21, which is guided movably, in particular longitudinally displaceably, in the outer shaft 22. At its front end, the outer shaft 22 has a multiplicity of orifice holes 25, which are arranged all the way round on the outer wall of the outer shaft 22. A rinsing liquid is guided back through the orifice holes 25.

At its distal end, the inner shaft 21 has a rectangular cutout 141 in which, by way of a fastening portion 140, a correspondingly configured end of an attachment 100 for tissue ablation is fitted, in particular welded. Adjoining this fastening portion 140, a rectilinear portion 130 extends parallel to the center line M of the inner shaft 21 as far as the distal end. The rectilinear portion 130 is adjoined by an angled or curved portion 110, which extends at an inclination relative to the rectilinear portion 130 and whose distal end forms an ablation edge 111 for tissue ablation.

In the embodiment according to FIG. 2a, the ablation edge 111 is rounded symmetrically at the sides. By means of this arrangement, an applied force can be concentrated in a small front region of the ablation edge 111. In particular, the ablation edge 111 can be curved uniformly and symmetrically. This embodiment is thus suitable as a device for precise ablation of tissue. In particular, tissue fragments can be removed in a targeted manner. The whole attachment 100 is accordingly (relatively) long, so as also to guide the ablation edge 111 far forward. For this purpose, the axial length of the attachment 100 for tissue ablation is in the range of between 1 mm and 16 mm, preferably in the range of between 3 mm and 13 mm, and more preferably in the range of between 5 mm and 11 mm.

In addition, a lateral ablation edge 113 can be provided on one of the two sides of the angled portion 110, or two corresponding ablation edges 113 can also be provided on both sides of the angled portion 110.

Figure 2B:
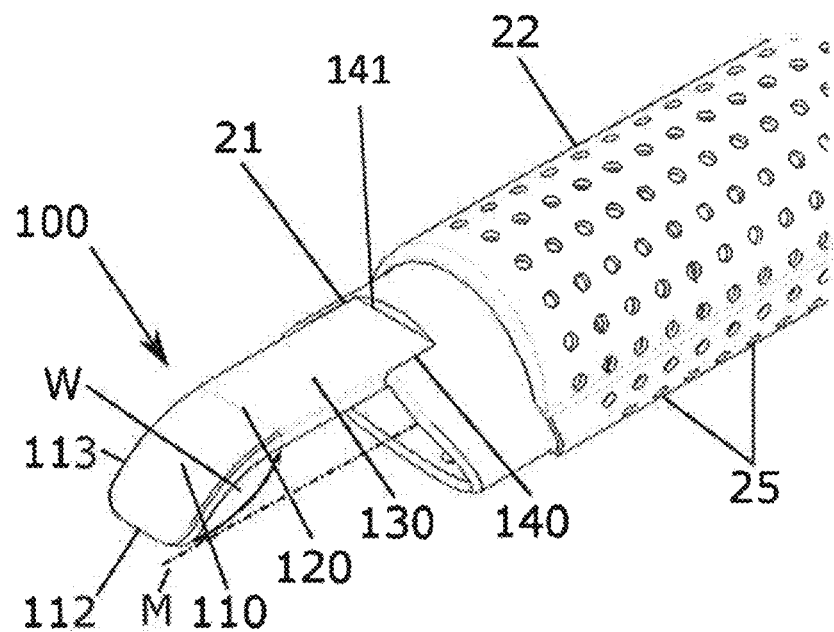
FIG. 2b shows a schematic view of the distal region of the medical instrument with a forwardly curved ablation edge according to FIG. 1.

FIG. 2b shows a detailed view of the distal end 10 of the embodiment according to FIG. 1, in which the shape of the angled portion 110 differs. According to FIG. 2b, the angled portion 110 has an ablation edge 112 which is rectilinear over the greater part and has lateral roundings at the distal end. Thus, a rectilinear ablation edge 112 is provided at the distal end of the angled portion 110. With this embodiment, the operator can apply a force over a wider surface. Therefore, this embodiment is also suitable for wide-reaching ablation of tissue. In this embodiment, the attachment can in particular be relatively short so as to make it controllable.

As in the above illustrative embodiment, at least one corresponding lateral ablation edge 113, with which tissue can likewise be separated, can be provided on the angled portion 110. In the aforementioned embodiments, the transition region between the rectilinear portion 130 and the angled portion 110 can in particular be arcuately curved.

As can be seen from FIGS. 2a and 2b, the curved or angled portion 110 encloses an angle W of between 115° and 155°, preferably of between 120° and 150°, more preferably of between 130° and 140°, with the rectilinear portion 130. The distal end of the inner shaft 21 can enclose a corresponding angle of between 25° and 65°, preferably of between 30° and 60° and more preferably of between 40° and 50° with a perpendicular to the center line M. The ablation edge 111, 112 extends substantially perpendicularly with respect to an underside of the distal end of the angled or arcuately curved portion 110, as a result of which tissue can be enucleated by axial adjustment of the medical instrument 1 since, in the axial adjustment, the ablation edge 111, 112 is displaced at an angle of approximately 45° over the tissue that is to be ablated. As can be seen from FIGS. 2a and 2b, the attachment 100 for tissue ablation extends radially inward by at most approximately 50% and preferably by at most approximately 40% of the internal diameter of the hollow outer shaft 22, such that any desired location in the axial continuation of the outer shaft can be reached by rotation of the outer shaft 22 about the center line. The attachment 100 is at all times arranged within an inner profile formed by the inner faces of the outer shaft 22, which in principle may be sufficient for inserting the distal end into a human body without damaging tissue, particularly if the attachment 100 does not protrude too far beyond the distal end of the inner shaft 21.

Figure 3A:
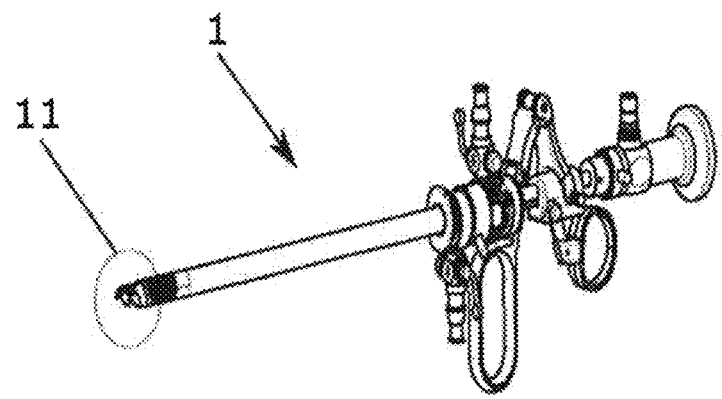
FIG. 3a shows a schematic view of a medical instrument with an additional HF coagulation attachment according to a further embodiment of the present invention.
Figure 3B:
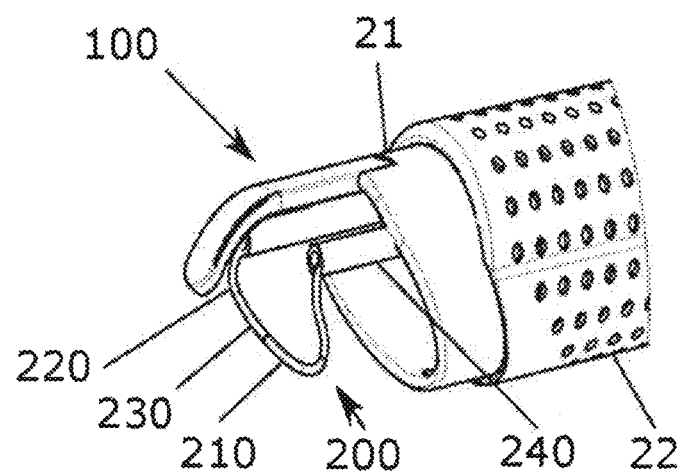
Figure 3C:
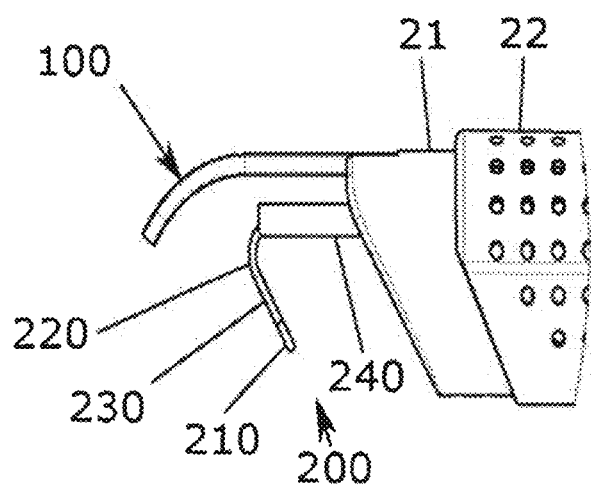

FIG. 3a shows a medical instrument 1 according to a further embodiment of the present invention, in which an HF coagulation attachment is additionally provided at the distal end 11, the details of which HF coagulation attachment are shown in the greatly enlarged views according to FIGS. 3b and 3c.

As is shown in FIG. 3b, an HF coagulation attachment 200 is moreover provided at the distal end of the inner shaft 21, proximally with respect to the attachment 100 for tissue ablation. The HF coagulation attachment 200 is formed here by a loop-shaped coil which can be subjected to a high-frequency voltage and which has a lower coil portion 210 and a central portion 230, the latter extending at an inclination with respect to the center line of the instrument and being connected via an upper connecting portion 220 to a current supply line 240. A high-frequency voltage can be applied to the HF coagulation attachment 200 via the current supply line. The current supply line 240 is electrically insulated from the inner shaft 21 and the hollow outer shaft 22, which applies also to the HF coagulation attachment 200.

The upper connecting portion 220 and the inclined, central connecting portion 230 both serve as connecting segments for the positioning of the arcuately curved coil portion 210. The actual tissue coagulation is carried out with the arcuately curved coil portion 210, if appropriate additionally with the inclined, central connecting portion 230, by means of a high-frequency voltage being applied to the coil.

FIG. 3c shows the distal end 11 according to FIG. 3b in a side view, where the axial and radial positions of the attachment 100 for tissue ablation are shown in relation to the HF coagulation attachment 200 and to the inner shaft 21. The attachment 100 for tissue ablation forms the outermost distal end of the medical instrument 1. The HF coagulation attachment 200 is proximally offset with respect to the attachment 100 for tissue ablation and, for tissue coagulation, protrudes axially from the inner shaft 21 less far than the attachment 100 for tissue ablation. Thus, the attachment 100 for tissue ablation in some ways protects the HF coagulation attachment 200 from mechanical damage, for example during the axial adjustment of the medical instrument 1 in the body tissue.

The attachment 100 for tissue ablation and the HF coagulation attachment 200 are also spaced apart from each other in the radial direction, in order to reliably provide electrical insulation. The HF coagulation attachment 200 and the attachment 100 for tissue ablation are both inclined downward, pointing toward the instrument center line of the medical instrument. While the HF coagulation attachment 200 slopes with the inclined, central portion 230 at an acute angle with respect to the instrument center line and points toward the distal end of the inner shaft 21, the attachment 100 for tissue ablation extends obliquely forward toward the distal end of the medical instrument. The attachment 100 for tissue ablation expediently does not extend beyond the instrument center line, whereas the HF coagulation attachment 200 expediently extends beyond it, as is shown in FIG. 3c. However, seen in a front view, the HF coagulation attachment 200 is also arranged within the profile of the inner shaft 21.

Of course, according to a preferred embodiment, only the attachment 100 for mechanical ablation of tissue may be provided, and the HF coagulation attachment 200 may be additionally advanced to the operation site if so required, for which purpose the medical instrument has a further instrument port. In this case, the HF coagulation attachment 200 can be arranged rigidly and axially immovably in the inner shaft 21. According to a preferred embodiment, the HF coagulation attachment 200 can if necessary be axially adjusted and/or rotated independently of the inner shaft 21, for example if tissue damage and/or bleeding is established via an optical insert introduced into the inner shaft 21, in order to be positioned exactly at the site of the damage and/or bleeding. To this end, the HF coagulation attachment 200 can be introduced as a separate insert into the inner shaft 21, for example together with the optical insert.

To ensure that the axial adjustment length of the HF coagulation attachment 200 is minimized, the inclined central connecting portion 230 preferably extends parallel to the distal end of the inner shaft 21, as is shown in FIG. 3c.

Figure 4A:
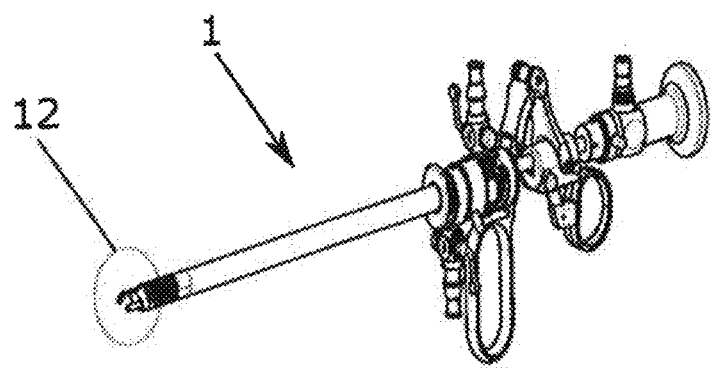
FIG. 4a shows a schematic view of a medical instrument with an additional laser coagulation attachment according to a further embodiment of the present invention.
Figure 4B:
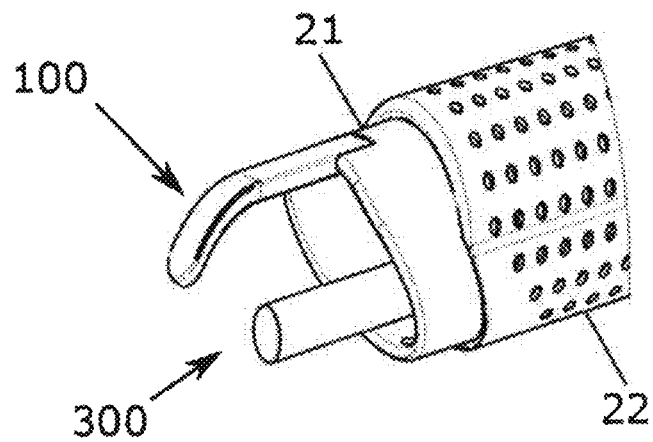
Figure 4C:
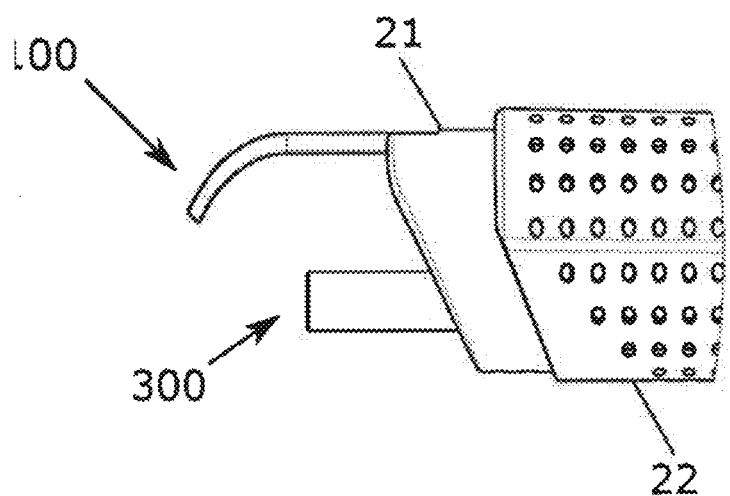

FIGS. 4a to 4c show a medical instrument 1 according to a further embodiment of the present invention having a laser coagulation attachment 300 in addition to the attachment 100 for tissue ablation.

As is shown in FIG. 4b, a laser coagulation attachment 300 is moreover provided at the distal end of the inner shaft 21, proximally with respect to the attachment 100 for tissue ablation. The laser coagulation attachment 300 in this case likewise protrudes from the inner shaft 21. In relation to the center line of the hollow outer shaft 22, the laser coagulation attachment 300 is arranged diametrically opposite the attachment 100 for mechanical tissue ablation. Thus, the attachment 100 for tissue ablation in some ways protects the laser coagulation attachment 300 from mechanical damage, for example during the axial adjustment of the medical instrument 1 in the body tissue. The laser coagulation attachment 300 can in particular be formed by the distal end of an optical fiber, which is routed to the distal end of the medical instrument 1 in order to coagulate tissue. For this purpose, the laser coagulation attachment 300 can in principle also be arranged inside the inner shaft 21, at the distal end thereof.

Of course, according to a preferred embodiment, only the attachment 100 for mechanical ablation of tissue may be provided, and the laser coagulation attachment 300 may be additionally advanced to the operation site if so required, for which purpose the medical instrument has a further instrument port. In this case, the laser coagulation attachment 300 can be arranged rigidly and axially immovably in the inner shaft 21. According to a preferred embodiment, the laser coagulation attachment 300 can if necessary be axially adjusted and/or rotated independently of the inner shaft 21, for example if tissue damage and/or bleeding is established via an optical insert introduced into the inner shaft 21, in order to be positioned exactly at the site of the damage and/or bleeding. To this end, the laser coagulation attachment 300 can be introduced as a separate insert into the inner shaft 21, for example together with the optical insert.

FIGS. 5a and 5b show a medical instrument 1 according to a further embodiment, in which the attachment 100 for tissue ablation can additionally be covered in order to prevent undesired tissue damage, for example during the insertion of the instrument attachment into human tissue, for example into a urethra for procedures on prostate tissue.

As is shown in FIG. 5b, a receiving element or closure piece 150 is provided at the distal end of the inner shaft 21 and can be axially adjusted relative to the inner shaft 21, as is indicated by the double arrow. The distal end of the receiving element 150 is dome-shaped. A cutout 151 is formed therein, corresponding to the shape of the attachment 100 for tissue ablation. In the deployed position according to FIG. 5a, the attachment 100 for tissue ablation is received in the cutout 151 at any rate to such an extent that its ablation edges are covered, in particular at the portion 111 as shown in FIG. 5b, as a result of which undesired tissue damage can be prevented, for example during the insertion of the instrument attachment into human tissue. A gentle insertion of the instrument attachment into human tissue is supported by the dome shape of the distal end of the receiving element 150.

The receiving element 150 can be retracted axially into the inner shaft 21 to such an extent that the attachment 100 for tissue ablation is exposed in order to ablate tissue, for example in order to enucleate human prostate tissue by means of the ablation edge 111, by axial adjustment of the inner shaft 21 or of the entire instrument attachment. The receiving element 150 can also be configured such that an HF coagulation attachment or a laser coagulation attachment is exposed in the retracted position, in order also to be able to coagulate tissue if necessary.

The receiving element 150 can in particular be configured as an obturator which completely closes the distal end of the instrument 1 during insertion into human tissue and thus sufficiently covers or receives the attachment 100 for tissue ablation but which can thereafter also be withdrawn completely from the hollow inner shaft 21, such that, for example, an optical insert, a coagulation insert, as described above, or other instruments can then be introduced into the hollow inner shaft 21.

For precise positioning of the instrument attachment, the inner shaft 21 is preferably guided rectilinearly relative to the outer shaft 22, i.e., during the axial adjustment of the inner shaft 21 relative to the outer shaft 22, the inner shaft 21 does not rotate in an uncontrolled manner. This can be achieved in principle by guide structures on the inner shaft 21 being in form-fit engagement with correspondingly shaped guide structures on the outer shaft 22, for example by the engagement of axially extending guide rails or guide strips. However, such rectilinear guiding is preferably obtained automatically through the profile of inner shaft 21 and outer shaft 22 itself, as is shown in FIGS. 6a to 7b.

Figure 6A:
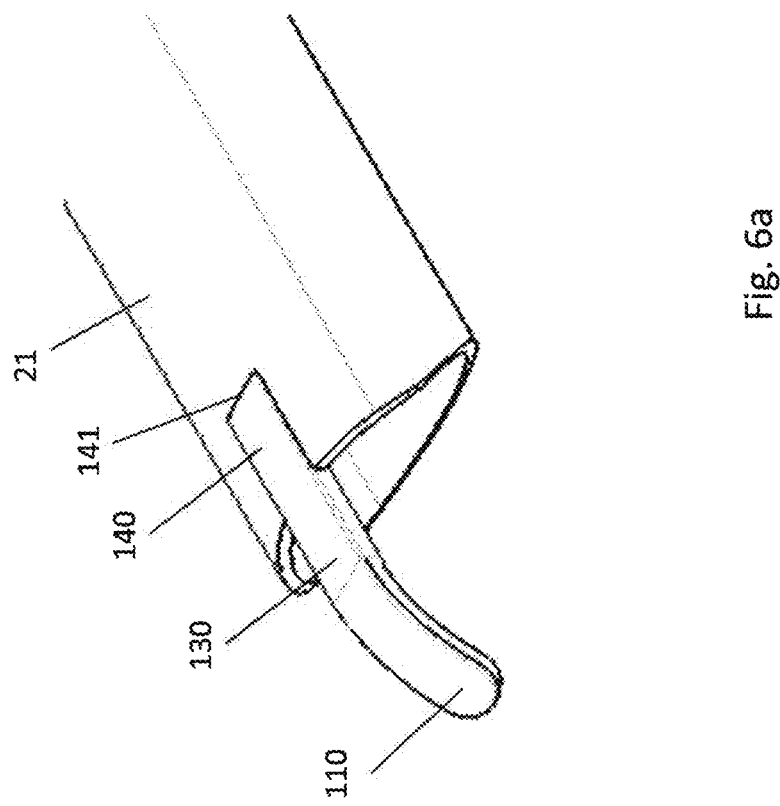
FIG. 6a shows a greatly enlarged perspective view of the distal region of a medical instrument according to a further embodiment of the present invention.
Figure 6B:
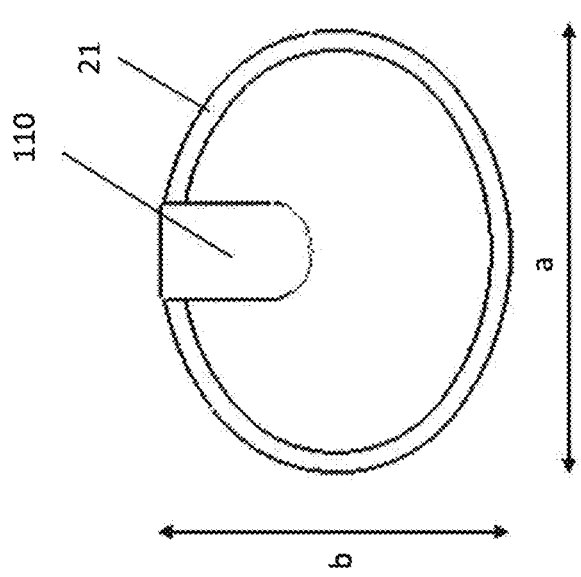
FIG. 6b shows the distal region of the medical instrument according to FIG. 6a in a front view.

According to FIG. 6b, the inner shaft 21 has an elliptic or oval profile, which is defined by a large semi-axis a and a small semi-axis b. The inner profile of the outer shaft (not shown) is designed corresponding to this. During the axial adjustment of the inner shaft 21 relative to the outer shaft, a rotation of the inner shaft is thereby reliably prevented.

Figure 7A:
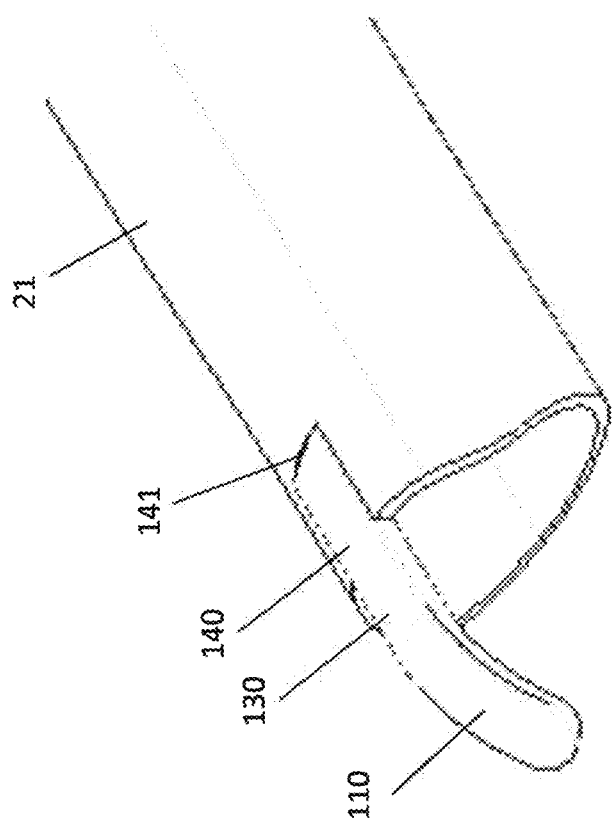
FIG. 7a shows a greatly enlarged perspective view of the distal region of a medical instrument according to a further embodiment of the present invention.
Figure 7B:
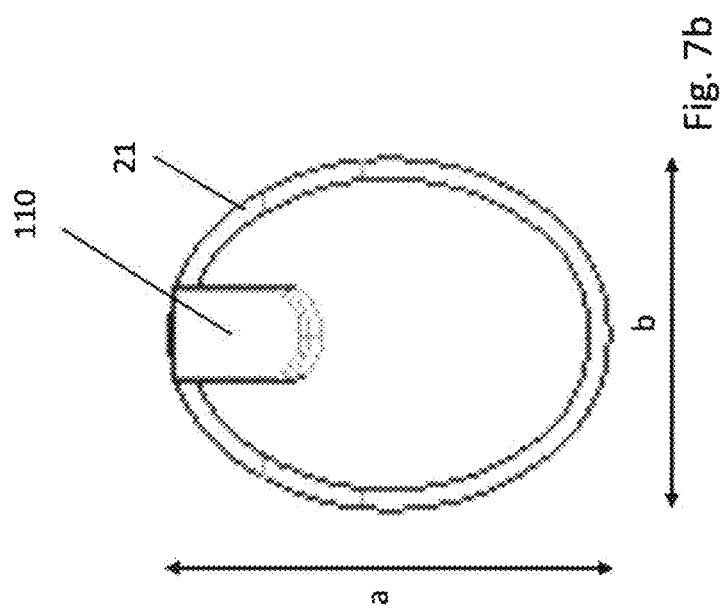
FIG. 7b shows the distal region of the medical instrument according to FIG. 7a in a front view.

In the illustrative embodiment according to FIGS. 7a and 7b, the orientations of the large semi-axis a and of the small semi-axis b are swapped around compared to the illustrative embodiment in FIGS. 6a and 6b, otherwise with the same position and orientation of the attachment 100 for tissue ablation.

The handling of the above-described medical instrument 1 during a surgical procedure is described below.

First of all, a medical instrument 1 is made available as described above with an attachment 100 for mechanical ablation of tissue, which attachment 100 is arranged directly at the distal end 10 of the inner shaft 21, wherein the attachment 100 is arranged within an inner profile formed by the inner faces of the outer shaft 22 and, in order to permit tissue ablation, the distal end of the inner shaft 21 protrudes axially beyond the distal end of the hollow outer shaft 22.

The shaft 20 is then inserted into the human tissue, in particular into a urethra, such that the attachment 100 for tissue ablation is positioned near the prostate. During the insertion, the attachment 100 for tissue ablation is sufficiently covered by or received within a receiving element 150, in particular an obturator. Thereafter, the receiving element 150 or the obturator is axially retracted to such an extent that the attachment 100 for tissue ablation is sufficiently exposed. By axial adjustment of the shaft 20, preferably of the inner shaft 21 together with the tissue ablation attachment 100 provided thereon, relative to the hollow outer shaft 22, the ablation edge of the attachment 100 is moved relative to the tissue, as a result of which a peeling or enucleating movement is executed for peeling off or enucleating tissue, in particular prostate tissue.

By the retraction or deployment of the receiving element 150 or obturator, an HF or laser coagulation attachment as described above can be sufficiently exposed in order to be able to perform tissue coagulation. For visual monitoring and control, a suitable lens system can in particular be guided through the hollow inner shaft 21 to the operating site.

After tissue has been ablated, the shaft 20 is withdrawn again from the human tissue in reverse sequence. Here, the attachment 100 for tissue ablation is advantageously once again sufficiently covered by or received in a receiving element 150, in particular an obturator, in order to prevent undesired tissue damage.

LIST OF REFERENCE SIGNS 1 medical instrument
10 distal end
11 distal end with HF coagulation attachment
12 distal end with laser coagulation attachment 20 shaft
21 inner shaft
22 outer shaft
23 receiving notch
25 orifice holes
30 control portion
31 positioning handle portion
32 positioning handle
35 operating handle portion
36 eyepiece
37 operating handle
100 attachment for tissue ablation
110 angled portion/arcuately curved portion
111 symmetrically curved ablation edge
112 (substantially) non-curved ablation edge
113 lateral ablation edges
120 angled separating or bending line
130 rectilinearly extending portion
140 fastening portion
141 cutout
150 obturator/receiving element
151 cutout/seat
200 HF coagulation attachment
210 lower end of HF coagulation coil
220 upper connecting portion
230 inclined/central portion of HF coagulation coil
240 current supply line
300 laser coagulation attachment
M instrument center line
W angle

We claim:

1. Medical instrument for tissue ablation by a minimally invasive surgical procedure, comprising
a hollow outer shaft,
an inner shaft configured as a hollow tube, and
a control portion at a proximal end of the medical instrument, in order to position the hollow outer shaft,
characterized in that
an attachment for mechanical ablation of tissue is arranged directly at a distal end of the inner shaft,
wherein the attachment does not protrude beyond an inner profile formed by inner faces of the outer shaft, and
wherein the distal end of the attachment protrudes axially beyond the distal end of the hollow outer shaft in order to ablate tissue, and
further comprising an elongate receiving element with a cutout or seat for temporarily receiving the attachment for mechanical ablation of tissue, wherein the elongate receiving element is axially adjustable relative to the inner shaft between a deployed position, in which the attachment for mechanical ablation of tissue is temporarily received in the cutout or seat, and a retracted position, in which the attachment for mechanical ablation of tissue protrudes axially beyond the distal end of the hollow outer shaft and is accessible for tissue ablation.

2. Medical instrument according to claim 1, wherein the attachment for mechanical ablation of tissue is connected to the distal end of the inner shaft via a rectilinearly extending portion, and a distal end of the attachment extends at an inclination to the rectilinear portion.

3. Medical instrument according to claim 2, wherein the rectilinear portion is adjoined by an arcuately curved portion or an angled portion at whose distal end an ablation edge is provided.

4. Medical instrument according to claim 3, wherein the curved or angled portion encloses an angle (W) of between 115° and 155°.

5. Medical instrument according to claim 3, wherein the ablation edge extends substantially perpendicularly with respect to an underside of the distal end of the angled or arcuately curved portion.

6. Medical instrument according to claim 3, wherein the ablation edge has a central portion which is not curved.

7. Medical instrument according to claim 3, wherein the ablation edge has a central portion which is curved symmetrically.

8. Medical instrument according to claim 1, wherein the axial length of the attachment for tissue ablation lies in the range of between 1 mm and 16 mm.

9. Medical instrument according to claim 1, wherein the attachment for tissue ablation extends radially inward by at most 50% of the internal diameter of the hollow outer shaft.

10. Medical instrument according to claim 1, wherein the attachment for mechanical ablation of tissue is welded onto the distal end of the inner shaft.

11. Medical instrument according to claim 1, wherein the inner shaft is guided longitudinally displaceably in the hollow outer shaft, and the control portion is moreover configured for adjusting the position of the inner shaft relative to the hollow outer shaft.

12. Medical instrument according to claim 11, wherein the control portion is coupled to the inner shaft such that the attachment can be retracted fully into the hollow outer shaft and, in order to permit tissue ablation, at least partially protrudes axially beyond a distal end of the hollow outer shaft.

13. Medical instrument according to claim 11, wherein the inner shaft is guided longitudinally displaceably and rectilinearly in the outer shaft.

14. Medical instrument according to claim 13, wherein an outer profile of the inner shaft is not rotationally symmetrical, being configured in particular as an oval or elliptical outer profile, and wherein an inner profile of the outer shaft is configured corresponding to the outer profile of the inner shaft in order to guide the inner shaft rectilinearly during an axial adjustment.

15. Medical instrument according to claim 14, wherein the coil to which the high-frequency voltage can be applied is axially adjustable relative to the inner shaft.

16. Medical instrument according to claim 1, wherein a coil to which a high-frequency voltage can be applied for tissue coagulation is moreover provided at the distal end of the inner shaft, which coil protrudes axially from the distal end of the inner shaft to a lesser extent than the attachment for mechanical ablation of tissue and is electrically insulated from the inner shaft.

17. Medical instrument according to claim 16, wherein the coil has a connecting portion and an arcuately curved loop at the distal end of the connecting portion, wherein the arcuately curved loop extends substantially parallel to the distal end of the inner shaft.

18. Medical instrument according to claim 1, wherein, seen in a side view of the distal end of the medical instrument, the arc-shaped loop and the distal end of the inner shaft extend at an inclination and toward the proximal end of the hollow inner shaft.

19. Medical instrument according to claim 1, wherein a laser coagulation attachment for tissue coagulation is moreover provided at the distal end of the inner shaft and protrudes axially from the distal end of the inner shaft.

20. Medical instrument according to claim 19, wherein the laser coagulation attachment protrudes from the distal end of the inner shaft less far than the attachment for mechanical ablation of tissue.

* * * * *